(12) United States Patent
Hwang et al.

(10) Patent No.: US 6,841,688 B2
(45) Date of Patent: Jan. 11, 2005

(54) METHOD OF PREPARING OPTICALLY PURE (R)- OR (S)- TETRAHYDROFURANYL KETONE

(75) Inventors: Hee-Jun Hwang, Daejeon (KR); Jong-Ho Lim, Daejeon (KR)

(73) Assignee: SK Corporation, Seoul (KR)

( * ) Notice: Subject to any disclaimer, the term of this patent is extended or adjusted under 35 U.S.C. 154(b) by 0 days.

(21) Appl. No.: 10/290,734

(22) Filed: Nov. 8, 2002

(65) Prior Publication Data

US 2003/0114693 A1 Jun. 19, 2003

(30) Foreign Application Priority Data

Dec. 4, 2001 (KR) ......................................... 2001-76279

(51) Int. Cl.$^7$ ............................................. C07D 307/02
(52) U.S. Cl. ....................................... 549/474; 549/487
(58) Field of Search ................................. 549/487, 474

(56) References Cited

U.S. PATENT DOCUMENTS 3,125,584 A * 3/1964 Weis et al. ................. 549/474

FOREIGN PATENT DOCUMENTS

| WO | WO 92/01696 | | 6/1992 | |
|---|---|---|---|---|
| WO | wo03014106 | * | 2/2003 | ................. 549/487 |

* cited by examiner

Primary Examiner—Rita Desai
Assistant Examiner—Raymond Covington
(74) Attorney, Agent, or Firm—Alston & Bird LLP

(57) ABSTRACT

Disclosed is a method of preparing an optically pure (R)- or (S)-tetrahydrofuranyl ketone. By such a method, (R)- or (S)-2-tetrahydrofuran amide is converted to (R)- or (S)-2-tetrahydrofuran nitrile through dehydration in the presence of a dehydrating agent and an amine base. Then, thus prepared (R)- or (S)-2-tetrahydrofuran nitrile is nucelophilic addition-reacted with a nucleophile, followed by hydrolyzing, thereby produce (R)- or (S)-tetrahydrofuranyl ketone having high optical purity, while minimizing production of other by-products.

12 Claims, No Drawings

METHOD OF PREPARING OPTICALLY PURE (R)- OR (S)- TETRAHYDROFURANYL KETONE

BACKGROUND OF THE INVENTION

1. Field of the Invention

The present invention pertains to methods of preparing (R)- or (S)-tetrahydrofuranyl ketones. More specifically, the present invention is directed to a method of preparing an industrially applicable (R)- or (S)-tetrahydrofuranyl ketone having high optical purity by dehydration of (R)- or (S)-2-tetrahydrofuran amide in the presence of a dehydrating agent and an amine base, to obtain (R)- or (S)-2-tetrahydrofuran nitrile, after which nucelophilic addition-reaction with a nucleophile and hydrolysis are carried out in order.

2. Description of the Prior Art

Generally, (R)- or (S)-tetrahydrofuranyl ketone compounds are widely employed for preparation of antibiotics which are used as antiviral medicines and of optically active chemicals, and also employed as important medicinal intermediates of optically active medicines and veterinary medicines.

However, most of the conventional techniques are directed to the production of racemic tetrahydrofuranyl ketones, rather than of optically pure (R)- or (S)-tetrahydrofuranyl ketones.

Meanwhile, WO 92/01696 discloses a method for preparation of (R)-2-acetyl-tetrahydrofuran bromide, in which a carboxylic acid moiety in (R)-2-tetrahydrofuroic acid used as a starting material is activated by oxalic acid chloride, and reacted with excessive diazomethane and then further with 48% aqueous hydrogen bromide solution, producing (R)-2-acetyl-tetrahydrofuran bromide. Also, a preparation method of 2-acetyl-tetrahydrofuran chlorides comprising reacting racemic 2-tetrahydrofuroic acid used as a starting material with diazomethane according to the same manner as in the above patent and further with hydrochloric acid, is described in J. Antibiot. 1994, 47(2), 253. But, the above methods cannot be applied on an industrial scale due to use of diazomethane being highly explosive.

In J. Heterocycl. Chem. 1995, 32(1), 109, a preparation method of tetrahydrofuranyl ketone is disclosed by reaction of racemic 2-tetrahydrofuroic acid and phenylmagnesium bromide or phenyllithium. However, this method is disadvantageous since even though (R)- or (S)-2-tetrahydrofuroic acid is employed as a starting material, the optical purity of the resultant tetrahydrofuranyl ketone is lowered due to racemization in the application on the industrial scale. Additionally, tertiary alcohols are produced in large amounts as by-products, thus making it difficult to apply the above method to production on the large scale.

Further, it is well known in the art that since ketones, resulting from a nucleophilic addition reaction of carboxylic acids, have higher activity for the nucleophilic addition than carboxylic acids used as a starting material, tertiary alcohols are produced in large amounts through additional nucleophilic addition reaction of said ketones, thus decreasing a reaction yield. Hence, diverse attempts have been conducted to overcome such problems.

For example, it is known that carboxylic acid and lithium hydride are reacted at a molar ratio of 1:1, to produce lithium carboxylate, which is then reacted with an organic lithium compound or a Grignard reagent, to prepare ketone. But, when this method is applied to preparation of an optically pure tetrahydrofuranyl ketone on an industrial scale, racemization occurs. So, the resultant ketone is low in optical purity.

Under these circumstances, there is proposed a preparation method in which carboxylic acid is converted, by use of N,O-dimethylhydroxyamine hydrochloride, to N,O-dimethyl hydroxiamide, followed by reacting with an organic lithium compound or a Grignard reagent to yield ketone. This method is advantageous in terms of suppression of tertiary alcohols produced as a by-product, but is disadvantageous due to use of expensive N,O-dimethylhydroxyamine hydrochloride. Therefore, it is difficult to industrially apply such a method, in terms of economic benefit. In particular, when this method is used for preparation of an optically pure tetrahydrofuranyl ketone on an industrial scale, racemization occurs, thus the produced ketone has low optical purity.

According to Tetrahedron Lett. 1984, 25(42), 4805, a method of preparing ketone is proposed, in which carboxylic acid is activated with thionyl chloride and reacted with a Grignard reagent in the presence of iron (III) catalyst to produce ketone. But, when such a method is also applied to preparation of an optically pure tetrahydrofuranyl ketone on an industrial scale, racemization is so unavoidable that the resultant ketone is low in optical purity.

SUMMARY OF THE INVENTION

Leading to the present invention, the intensive and thorough research into methods for preparation of (R)- or (S)-tetrahydrofuranyl ketone, carried out by the present inventors aiming to avoid the problems encountered in the prior arts, resulted in the finding that, when (R)- or (S)-2-tetrahydrofuran amide is used a starting material, (R)- or (S)-2-tetrahydrofuran nitrile obtained from dehydration of the above starting material is nucleophilic addition-reacted with a nucleophile, followed by hydrolyzing to yield (R)- or (S)-tetrahydrofuranyl ketone having high optical purity.

Therefore, it is an object of the present invention to provide a method of preparing an industrially applicable (R)-tetrahydrofuranyl ketone having high optical purity.

It is another object of the present invention to provide a method of preparing an industrially applicable (S)-tetrahydrofuranyl ketone having high optical purity.

In accordance with an embodiment of the present invention, there is provided a method of preparing an optically pure (R)-tetrahydrofuranyl ketone, which comprises:

dehydrating (R)-2-tetrahydrofuran amide, represented by the following chemical formula 1a, in the presence of a dehydrating agent and an amine base at 50 to 100° C. for 2 to 6 hours to obtain (R)-2-tetrahydrofuran nitrile represented by the following chemical formula 2a;

nucelophilic addition-reacting the (R)-2-tetrahydrofuran nitrile with a nucleophile in an organic solvent at the temperature range of from −80 to 100° C. for 10 minutes to 4 hours, followed by hydrolyzing by use of aqueous acidic solution to produce (R)-tetrahydrofuranyl ketone represented by the following chemical formula 3a; and recovering the resulting product obtained from the previous step:

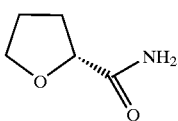

Chemical Formula 1a

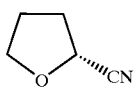

Chemical Formula 2a

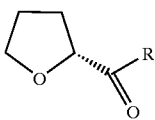

Chemical Formula 3a wherein, R is a straight-chained or branched, saturated or unsaturated aliphatic alkyl group having 1–30 carbon atoms; a saturated or unsaturated, substituted or unsubstituted cyclic alkyl group having 3–30 carbon atoms; or a substituted or unsubstituted aryl group having 6–30 carbon atoms.

In accordance with another embodiment of the present invention, there is provided a method of preparing an optically pure (S)-tetrahydrofuranyl ketone, which comprises:

dehydrating (S)-2-tetrahydrofuran amide represented by the following chemical formula 1b, in the presence of a dehydrating agent and an amine base at 50 to 100° C. for 2 to 6 hours to obtain (S)-2-tetrahydrofuran nitrile represented by the following chemical formula 2b; and nucelophilic addition-reacting the (S)-2-tetrahydrofuran nitrile with a nucleophile in an organic solvent at the temperature range of from −80 to 100° C. for 10 minutes to 4 hours, followed by hydrolyzing by use of aqueous acidic solution to produce (S)-tetrahydrofuranyl ketone represented by the following chemical formula 3b; and recovering the resulting product obtained from the previous step:

Chemical Formula 1b

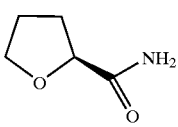

Chemical Formula 2b

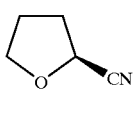

Chemical Formula 3b

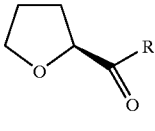

wherein, R is a straight-chained or branched, saturated or unsaturated aliphatic alkyl group having 1–30 carbon atoms; a saturated or unsaturated, substituted or unsubstituted cyclic alkyl group having 3–30 carbon atoms; or a substituted or unsubstituted aryl group having 6–30 carbon atoms.

DETAILED DESCRIPTION OF THE INVENTION

The present invention is directed to a preparation method of an optically pure (R)- or (S)-tetrahydrofuranyl ketone. Initially, (R)- or (S)-2-tetrahydrofuran amide is dehydrated in the presence of a dehydrating agent and an amine base to produce (R)- or (S)-2-tetrahydrofuran nitrile. Thereafter, the (R)- or (S)-2-tetrahydrofuran nitrile is nucleophilic addition-reacted with a nucleophile, followed by hydrolysis. As a result, (R)- or (S)-tetrahydrofuranyl ketone is produced with high optical purity.

According to the present invention, (R)-2-tetrahydrofuran amide of chemical formula 1a or (S)-2-tetrahydrofuran amide of the following chemical formula 1b is used as a starting material:

Chemical Formula 1a

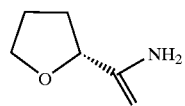

Chemical Formula 1b

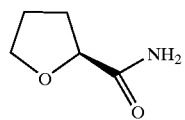

In the present invention, the (R)- or (S)-2-tetrahydrofuran amide is preferably dehydrated in the presence of 1.0–1.5 equivalents dehydrating agent and 1.0–7.0 equivalents amine base under conditions of a reaction temperature ranging from 50 to 100° C. and a period of time required for reaction ranging from 2 to 6 hours, to produce (R)-2-tetrahydrofuran nitrile represented by the following chemical formula 2a or (S)-2-tetrahydrofuran nitrile represented by the following chemical formula 2b:

Chemical Formula 2a

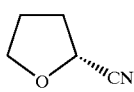

Chemical Formula 2b

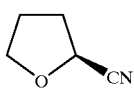

As such, it is noted that each using amount of the dehydrating agent and the amine base should be adjusted in proper range. For example, in case of falling out of the range as above, the dehydration may not sufficiently performed or wastes may excessively generated. Furthermore, if the period of time required for reaction is shorter than 2 hours, reaction conversion efficiency becomes low. On the other hand, if the reaction time is longer than 6 hours, economic benefit is not realized due to insufficiently long reaction time. Also, when the reaction temperature is lower than 50° C., a period of time required to obtain the reaction conversion efficiency of 100% is lengthened. Meanwhile, the temperature higher than 100° C. leads to generation of large amounts of by-products.

The amine base of the present invention is selected from the group consisting of primary amines, such as methylamine, ethylamine, propylamine, butylamine, etc.; secondary amines, such as dimethylamine, diethylamine, diisopropylamine, etc.; tertiary amines, such as trimethylamine, triethylamine, diethylisopropylamine, etc.; and pyridine. Among them, pyridine is preferably used.

The dehydrating agent of the present invention is selected from the group consisting of thionyl chloride, para-toluenesulfone chloride, phosphorous pentoxide, phosphorous oxytrichloride, a mixture of dimethylsulfoxide and oxalic acid chloride, trifluoroacetic anhydride, and a mixture of formaldehyde and formic acid. Among them, para-toluenesulfone chloride is preferably used.

Then, each of (R)- and (S)-2-tetrahydrofuran nitrile, resulting from the above dehydration, is nucleophilic addition-reacted with a nucleophile. Then, hydrolysis is carried out to obtain (R)-tetrahydrofuranyl ketone represented by the following chemical formula 3a, or (S)-tetrahydrofuranyl ketone represented by the following chemical formula 3b:

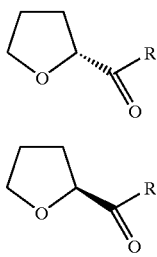

Chemical Formula 3a

Chemical Formula 3b wherein, R is a straight-chained or branched, saturated or unsaturated aliphatic alkyl group having 1–30 carbon atoms; a saturated or unsaturated, substituted or unsubstituted cyclic alkyl group having 3–30 carbon atoms; or a substituted or unsubstituted aryl group having 6–30 carbon atoms.

As for the nucleophic addition reaction, (R)- or (S)-2-tetrahydrofuran nitrile and the nucleophile are slowly introduced in the presence of an organic solvent. At this time, the (R)- or (S)-2-tetrahydrofuran nitrile and the nucleophile are introduced at an equivalent ratio of 1:1–1:3, preferably 1:1.1–1:2, and most preferably 1:1.1–1:1.3. When the ratio is less than 1:1, a part of the nucleophile is reacted with water and other impurities in the organic solvent and thus the reaction conversion efficiency is decreased. On the other hand, when the ratio exceeds 1:3, large amounts of the nucleophile remain unreacted, thus not generating economic benefit.

Examples of the nucleophile useful in the present invention include, but are not limited to, Grignard reagents, such as methylmagnesium chloride, methylmagnesium bromide, methylmagnesium iodide, ethylmagnesium chloride, ethylmagnesium bromide, ethylmagnesium iodide, n-propylmagnesium chloride, n-propylmagnesium bromide, n-propylmagnesium iodide, iso-propylmagnesium chloride, iso-propylmagnesium bromide, iso-propylmagnesium iodide, cyclopentylmagnesium chloride, cyclohexylmagnesium chloride, cyclopentylmagnesium bromide, cyclohexylmagnesium bromide, cyclopentylmagnesium iodide, cyclohexylmagnesium iodide, propargylmagnesium bromide, vinylmagnesium chloride, vinylmagnesium bromide, phenylmagnesium chloride, phenylmagnesium bromide and phenylmagnesium iodide; organic lithium compounds, such as methyllithium, ethyllithium, propyllithium, iso-propyllithium, n-butyllithium, iso-butyllithium, neobutyllithium and phenyllithium; organic zinc compounds, such as dimethylzinc and diethylzinc; and organic aluminum compounds, such as trimethylaluminum and triethylaluminum.

As the organic solvent, suitable is diethylether, di-n-butylether, methylneobutylether, isopropylether, tetrahydrofuran, 1,4-dioxane, n-hexane, n-heptane, benzene, toluene, xylene, or mixtures thereof. Preferably, the organic solvent is diethylether, dibutylether, methylneobutylether, isopropylether, tetrahydrofuran, 1,4-dioxane, or mixtures thereof. Most preferably, tetrahydrofuran is used.

The nucleophilic addition reaction is performed in the temperature range of −80 to 100° C., preferably −20 to 50° C., and most preferably 0 to 30° C. The reaction temperature lower than −80° C. causes the reduction of economic benefits due to the increased reaction time. Meanwhile, the temperature higher than 100° C. results in lowered optical purity due to racemization of the product.

In addition, the nucleophilic addition is conducted for 10 minutes to 4 hours, preferably for 10 minutes to 2 hours, and most preferably for 30 minutes to 1 hour. If the time is shorter than 10 minutes, the reaction conversion efficiency is reduced. On the other hand, if the time is longer than 4 hours, economic benefit is not realized due to excessively lengthened time.

After completion of the nucleophilic addition, hydrolysis is performed using an acidic aqueous solution to effectively prepare (R)- or (S)-tetrahydrofuranyl ketone, without any change of optical purity.

As described above, the present invention is advantageous in that (R)- or (S)-tetrahydrofuran nitrile is used, instead of conventionally used (R)- or (S)-2-tetrahydrofuroic acid, whereby the amount of the nucleophile to be used can be decreased by 1 equivalent or more, thus realizing economic benefits. As well, without any decrease of optical purity, (R)- or (S)-tetrahydrofuranyl ketone can be obtained while production of tertiary alcohols as a by-product is minimized.

Having generally described this invention, a further understanding can be obtained by reference to certain specific examples which are provided herein for purposes of illustration only and are not intended to be limiting unless otherwise specified.

EXAMPLE 1

195 g of pyridine was introduced into a 1 L reactor and stirred, to which 40.5 g of (S)-2-tetrahydrofuran amide having an optical purity of 99.1% ee was added together with 73.8 g of para-toluene sulfone chloride, and the reaction was conducted at 50° C. for 2 hours with stirring. Thereafter, most of the pyridine was removed through concentration under reduced pressure. The reactor was placed into a water bath filled with ice water, and added with dilute hydrochloric acid and stirred. Then, dichloromethane was added thereto for extraction, followed by removing an aqueous layer. Dichloromethane in the extracted organic layer was removed under reduced pressure and the dichloromethane-removed organic layer was distilled off under vacuum, yielding 25 g of (S)-2-tetrahydrofuran nitrile.

A 0.5 L reactor at a temperature of 0° C. was added with 0.1 L of 3 M methylmagnesium chloride in tetrahydrofuran, to which 25 g of (S)-2-tetrahydrofuran nitrile as previously obtained, in 0.07 L of tetrahydrofuran was slowly added dropwise. As such, the reaction was carried out for 0.5 hours with stirring, while the temperature within the reactor was controlled below 15° C. Next, the resulting solution was added dropwise to 32 g of concentrated hydrochloric acid in 0.2 L of water, while the temperature of the reaction was controlled below 25° C. Thereafter, the extraction was conducted by use of ethylacetate, followed by removing the solvent therein under reduced pressure, and the remainder was vacuum distilled off to produce 17.7 g of (S)-2-acetyl-tetrahydrofuran having an optical purity of 99.1% ee.

EXAMPLE 2

A 0.5 L reactor was added with 70 g of pyridine and stirred, and then added with 20 g of (R)-2-tetrahydrofuran amide having an optical purity of 98.5% ee and 37 g of para-toluenesulfone chloride, and stirred at 50° C. for 2 hours. Thereafter, most of the pyridine was removed through concentration under reduced pressure.

Then, the reactor was placed into a water bath filled with ice water, and added with dilute hydrochloric acid and stirred. Then, dichloromethane was added thereto for extraction, followed by removing an aqueous layer. Dichloromethane in the extracted organic layer was removed under reduced pressure and the dichloromethane-removed organic layer was vacuum distilled off, yielding 13.5 g of (R)-2-tetrahydrofuran nitrile.

A 1 L reactor at a temperature of 0° C. was added with 0.4 L of 1.6 M n-butyllithium in n-hexane, to which 13.5 g of (R)-2-tetrahydrofuran nitrile as previously obtained, in 0.07 L of tetrahydrofuran was slowly added dropwise. As such, the reaction was carried out for 1 hour with stirring, while the temperature within the reactor was controlled below 15° C. Next, the resulting solution was added dropwise to 65 g of concentrated hydrochloric acid in 0.4 L of water, while the temperature of the reaction was controlled below 25° C. Thereafter, the extraction was conducted by use of ethylacetate, followed by removing the solvent therein under reduced pressure, and the remainder was vacuum distilled off to produce 19.6 g of (R)-1-(2-tetrahydrofuranyl)-1-pentanone having an optical purity of 98.5% ee.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method of preparing an optically pure (R)-tetrahydrofuranyl ketone, which comprises the following steps of:

dehydrating (R)-2-tetrahydrofuran amide, represented by the following chemical formula 1a, in the presence of a dehydrating agent and an amine base at 50 to 100° C. for 2 to 6 hours to obtain (R)-2-tetrahydrofuran nitrile represented by the following chemical formula 2a;

nucelophilic addition-reacting (R)-2-tetrahydrofuran nitrile with a nucleophile in an organic solvent at the temperature range of −80 to 100° C. for 10 minutes to 4 hours, followed by hydrolyzing by use of aqueous acidic solution to produce (R)-tetrahydrofuranyl ketone represented by the following chemical formula 3a; and recovering the resulting product obtained from the previous step:

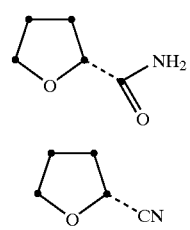

Chemical Formula 1a

Chemical Formula 2a

-continued

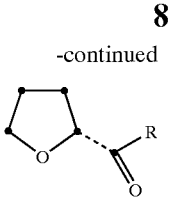

Chemical Formula 3a wherein, R is a straight-chained or branched, saturated or unsaturated aliphatic alkyl group having 1–30 carbon atoms; a saturated or unsaturated, substituted or unsubstituted cyclic alkyl group having 3–30 carbon atoms; or a substituted or unsubstituted aryl group having 6–30 carbon atoms.

2. The method as defined in claim 1, wherein said dehydrating agent is selected from the group consisting of thionyl chloride, para-toluenesulfone chloride, phosphorous pentoxide, phosphorous oxytrichloride, a mixture of dimethylsulfoxide and oxalic acid chloride, trifluoroacetic anhydride, and a mixture of formaldehyde and formic acid.

3. The method as defined in claim 1, wherein said amine base is selected from the group consisting of methylamine, ethylamine, propylamine, butylamine, dimethylamine, diethylamine, diisopropylamine, trimethylamine, triethylamine, diethylisopropylamine, and pyridine.

4. The method as defined in claim 1, wherein said nucleophile is selected from the group consisting of Grignard reagent, organic lithium compound, organic zinc compound and organic aluminum compound.

5. The method as defined in claim 4, wherein said Grignard reagent is methylmagnesium chloride, methylmagnesium bromide, methylmagnesium iodide, ethylmagnesium chloride, ethylmagnesium bromide, ethylmagnesium iodide, n-propylmagnesium chloride, n-propylmagnesium bromide, n-propylmagnesium iodide, iso-propylmagnesium chloride, iso-propylmagnesium bromide, iso-propylmagnesium iodide, cyclopentylmagnesium chloride, cyclohexylmagnesium chloride, cyclopentylmagnesium bromide, cyclohexylmagnesium bromide, cyclopentylmagnesium iodide, cyclohexylmagnesium iodide, propargylmagnesium bromide, vinylmagnesium chloride, vinylmagnesium bromide, phenylmagnesium chloride, phenylmagnesium bromide or phenylmagnesium iodide; said organic lithium compound is methyllithium, ethyllithium, propyllithium, iso-propyllithium, n-butyllithium, iso-butyllithium, neobutyllithium or phenyllithium; said organic zinc compound is dimethylzinc or diethylzinc; and said organic aluminum compound is trimethylaluminum or triethylaluminum.

6. The method as defined in claim 1, wherein said organic solvent is selected from the group consisting of diethylether, di-n-butylether, methylneobutylether, isopropylether, tetrahydrofuran, 1,4-dioxane, n-hexane, n-heptane, benzene, toluene, xylene and mixtures thereof.

7. A method of preparing an optically pure (S)-tetrahydrofuranyl ketone, which comprises the following steps of:

dehydrating (S)-2-tetrahydrofuran amide, represented by the following chemical formula 1b, in the presence of a dehydrating agent and an amine base at 50 to 100° C. for 2 to 6 hours to obtain (S)-2-tetrahydrofuran nitrile represented by the following chemical formula 2b;

nucelophilic addition-reacting the (S)-2-tetrahydrofuran nitrile with a nucleophile in an organic solvent at the temperature range of −80 to 100° C. for 10 minutes to 4 hours, followed by hydrolyzing by use of aqueous acidic solution to produce (S)-tetrahydrofuranyl ketone represented by the following chemical formula 3b; and recovering the resulting product obtained from the previous step:

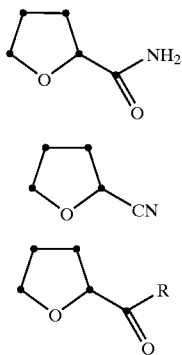

Chemical Formula 1b

Chemical Formula 2b

Chemical Formula 3b wherein, R is a straight-chained or branched, saturated or unsaturated aliphatic alkyl group having 1–30 carbon atoms; saturated or unsaturated, substituted or unsubstituted cyclic alkyl group having 3–30 carbon atoms; or a substituted or unsubstituted aryl group having 6–30 carbon atoms.

8. The method as defined in claim 7, wherein said dehydrating agent is selected from the group consisting of thionyl chloride, para-toluenesulfone chloride, phosphorous pentoxide, phosphorous oxytrichloride, a mixture of dimethylsulfoxide and oxalic acid chloride, trifluoroacetic anhydride, and a mixture of formaldehyde and formic acid.

9. The method as defined in claim 7, wherein said amine base is selected from the group consisting of methylamine, ethylamine, propylamine, butylamine, dimethylamine, diethylamine, diisopropylamine, trimethylamine, triethylamine, diethylisopropylamine, and pyridine.

10. The method as defined in claim 7, wherein said nucleophile is selected from the group consisting of Grignard reagent, organic lithium compound, organic zinc compound and organic aluminum compound.

11. The method as defined in claim 10, wherein said Grignard reagent is methylmagnesium chloride, methylmagnesium bromide, methylmagnesium iodide, ethylmagnesium chloride, ethylmagnesium bromide, ethylmagnesium iodide, n-propylmagnesium chloride, n-propylmagnesium bromide, n-propylmagnesium iodide, iso-propylmagnesium chloride, iso-propylmagnesium bromide, iso-propylmagnesium iodide, cyclopentylmagnesium chloride, cyclohexylmagnesium chloride, cyclopentylmagnesium bromide, cyclohexylmagnesium bromide, cyclopentylmagnesium iodide, cyclohexylmagnesium iodide, propargylmagnesium bromide, vinylmagnesium chloride, vinylmagnesium bromide, phenylmagnesium chloride, phenylmagnesium bromide or phenylmagnesium iodide; said organic lithium compound is methyllithium, ethyllithium, propyllithium, iso-propyllithium, n-butyllithium, iso-butyllithium, neobutyllithium or phenyllithium; said organic zinc compound is dimethylzinc or diethylzinc; and said organic aluminum compound is trimethylaluminum or triethylaluminum.

12. The method as defined in claim 7, wherein said organic solvent is selected from the group consisting of diethylether, di-n-butylether, methylneobutylether, isopropylether, tetrahydrofuran, 1,4-dioxane, n-hexane, n-heptane, benzene, toluene, xylene and mixtures thereof.

* * * * *